(12) United States Patent
Khulusi et al.

(10) Patent No.: US 7,681,042 B2
(45) Date of Patent: Mar. 16, 2010

(54) SYSTEM AND METHOD FOR DIS-IDENTIFYING SENSITIVE INFORMATION AND ASSOCIATED RECORDS

(75) Inventors: Bassam Khulusi, Overland Park, KS (US); Ognjen Vasic, Lenexa, KS (US)

(73) Assignee: Eruces, Inc., Lenexa, KS (US)

( * ) Notice: Subject to any disclaimer, the term of this patent is extended or adjusted under 35 U.S.C. 154(b) by 1428 days.

(21) Appl. No.: 10/871,179

(22) Filed: Jun. 17, 2004

(65) Prior Publication Data

US 2005/0283620 A1    Dec. 22, 2005

(51) Int. Cl.
*H04K 1/00* (2006.01)
(52) U.S. Cl. ...................................................... 713/185
(58) Field of Classification Search .................. 713/185; 380/277
See application file for complete search history.

(56) References Cited

U.S. PATENT DOCUMENTS

| | | | |
|---|---|---|---|
| 4,423,287 | A | 12/1983 | Zeidler |
| 4,578,530 | A | 3/1986 | Zeidler |
| 4,757,534 | A | 7/1988 | Matyas |
| 4,912,762 | A | 3/1990 | Lee |
| 5,301,270 | A | 4/1994 | Steinberg |
| 5,319,705 | A | 6/1994 | Halter |
| 5,363,507 | A | 11/1994 | Nakayama |
| 5,369,702 | A | 11/1994 | Shanton |
| 5,495,533 | A | 2/1996 | Linehan |

(Continued)

FOREIGN PATENT DOCUMENTS

EP    0 884 670 A1    2/1998

(Continued)

OTHER PUBLICATIONS

Churches, Tim; "A proposed architecture and method of operation for improving the protection of privacy and confidentiality in disease registers"; BMC Medical Research Methodology, Biomed Central, London, GB, vol. 3, No. 1; Jan. 6, 2003, pp. 1-13.

*Primary Examiner*—Jung Kim
*Assistant Examiner*—Samson B Lemma
(74) *Attorney, Agent, or Firm*—Spencer Fane Britt & Browne LLP

(57) ABSTRACT

A computer-based system (10) and method for dis-identifying personal identifiable information (152, 162) and associated records (172) is disclosed. The system includes a system manager (20) module, an encryption and key management module (30), and a storage module (40). The system manager module (20) stores related sensitive information portions (152) of the personal identifiable information (152, 162), non-sensitive information portions (162) of the personal identifiable information, and associated records (172) in separate databases (100, 110, 120 or 150, 160, 170) in storage module (40) with each database record including one or more hidden links generated by the encryption and key management module (30) that can be used to determine the related records or information in one of the other databases. The hidden links are encrypted so that the relationships between the database records are hidden. The methods provide for storing sensitive and non-sensitive personal identifiable information and associated records as database records, and for storing the hidden links associated with these database records. The present invention also includes methods for retrieving sensitive personal identifiable information for a given associated record and for retrieving the associated record(s) for a given sensitive personal identifiable information.

22 Claims, 9 Drawing Sheets

U.S. PATENT DOCUMENTS

| | | | |
|---|---|---|---|
| 5,533,123 | A | 7/1996 | Force |
| 5,546,304 | A | 8/1996 | Marschner |
| 5,625,693 | A | 4/1997 | Rohatgi |
| 5,680,452 | A | 10/1997 | Shanton |
| 5,682,524 | A | 10/1997 | Freund |
| 5,729,608 | A | 3/1998 | Janson |
| 5,757,925 | A | 5/1998 | Faybishenko |
| 5,764,772 | A | 6/1998 | Kaufman |
| 5,778,072 | A | 7/1998 | Samar |
| 5,796,830 | A | 8/1998 | Johnson |
| 5,809,497 | A | 9/1998 | Freund |
| 5,815,573 | A | 9/1998 | Johnson |
| 5,870,468 | A | 2/1999 | Harrison |
| 5,907,618 | A | 5/1999 | Gennaro |
| 5,915,025 | A | 6/1999 | Taguchi |
| 5,937,066 | A | 8/1999 | Gennaro |
| 5,949,882 | A | 9/1999 | Angelo |
| 6,044,154 | A | 3/2000 | Kelly |
| 6,051,469 | A | 4/2000 | Sheu et al. |
| 6,058,188 | A | 5/2000 | Chandersekaran |
| 6,084,969 | A | 7/2000 | Wright |
| 6,148,342 | A * | 11/2000 | Ho ............................... 709/225 |
| 6,199,113 | B1 | 3/2001 | Alegre |
| 6,249,866 | B1 | 6/2001 | Brundrett |
| 6,289,451 | B1 | 9/2001 | Dice |
| 6,449,621 | B1 * | 9/2002 | Pettovello ................. 707/104.1 |
| 6,785,810 | B1 * | 8/2004 | Lirov et al. .................. 713/165 |
| 7,315,859 | B2 * | 1/2008 | Samar ........................... 707/9 |
| 2001/0019614 | A1 * | 9/2001 | Madoukh .................... 380/277 |
| 2003/0021417 | A1 * | 1/2003 | Vasic et al. .................. 380/277 |
| 2003/0208686 | A1 * | 11/2003 | Thummalapally et al. ... 713/193 |
| 2004/0143745 | A1 | 7/2004 | Margolus |
| 2006/0143268 | A1 * | 6/2006 | Chatani ....................... 709/203 |

FOREIGN PATENT DOCUMENTS

| | | |
|---|---|---|
| FR | 2810434 | 12/2001 |
| JP | 11143780 | 5/1999 |
| WO | WO 97/49211 | 12/1997 |
| WO | WO 01/35226 A1 | 5/2001 |
| WO | WO 02/29577 A2 | 4/2002 |

* cited by examiner

SPII Table                 ←150

| SPII – multiple columns 152 | HL$_{Di}$  154 |
|---|---|
|  |  |

NSPII Table                ←160

| E$_{Di}$ (HL$_{Di}$) 164 | E$_{Ri}$ (HL$_{Di}$) 166 | HL$_{Ri}$ 168 | NSPII – multiple columns 162 |
|---|---|---|---|
|  |  |  |  |

AR Table                   ←170

| E$_{Di}$ (HL$_{Di}$) 174 | ARI – multiple columns 172 |
|---|---|
|  |  |

150  PATIENT TABLE (Sensitive Information)

| Name 152a | Address 152b | SS# 152c | DOB 152d | HL$_{Di}$ 154 |
|---|---|---|---|---|
| Jones, Arlene | 116 E. Mulberry | 555-55-555 | 08-01-31 | ACEx0aZG1CpDv.... |
| | | | | |
| | | | | |

160  PATIENT TABLE (Non-sensitive Information)

| E$_{Di}$ | E$_{Ri}$ 166 | HL$_{Ri}$ 168 | Sex 162a | Age 162b | M/S 162c | Race 162d |
|---|---|---|---|---|---|---|
| kXE3sFcE+Jx... | GxlNhfUZ/ufCP... | ACEx0aZG1CpDv.... | F | 73 | W | Hispanic |
| | | | | | | |
| | | | | | | |

170  PRESCRIPTION TABLE

| E$_{Di}$ 174 | Date 172a | Rx 172b | Strength 172c | Dose 172d | Quanity 172e |
|---|---|---|---|---|---|
| kXE3sFcE+Jx... | 05-11-04 | Valium | 10 mg | 1 Tab q 12 hrs | #10 |
| | | | | | |
| | | | | | |

SYSTEM AND METHOD FOR DIS-IDENTIFYING SENSITIVE INFORMATION AND ASSOCIATED RECORDS

CROSS REFERENCE TO RELATED APPLICATIONS

None.

STATEMENT REGARDING FEDERALLY SPONSORED RESEARCH AND DEVELOPMENT

None.

BACKGROUND OF THE INVENTION

The present invention relates generally to a system and method for storing information in a computer system. More specifically, the present invention encompasses a system and method for storing personal identifiable information and associated records in a computer system in which the personal identifiable information and the associated records are stored separately and any link between the information and records is hidden.

Computer or cyber crime is a fact of life in today's business environment especially with the proliferation of Internet use. Many businesses have suffered security breaches of one form or another and, as a result, have suffered both tangible and intangible losses. Significantly, security breaches have lead to the loss of both proprietary and sensitive or confidential information. Losses of this type have cost companies money, have tarnished corporate images, and have caused the disruption of business. In addition, several recent government regulations, such as HIPAA and the Gramm-Leach Act, require data confidentiality to ensure consumer privacy. Failure to comply with these regulations, that is allowing the disclosure of confidential consumer information, could result in a company receiving a significant fine or prevent a company from qualifying for certain contracts.

Thus, improving and/or maintaining the security of the information stored on its computer system or network is a high priority for many businesses. For example, because of HIPAA, businesses in the medical profession or businesses that deal with the medical profession must ensure the confidentiality of patient information and records. Patient information may include sensitive information such as the patient's name, address, telephone number, and social security number, and non-sensitive information such as the patient's gender, height, weight, race, and marital status. Similarly, the link between a patient's information and the patient's records, which might include information concerning prescriptions, diseases or doctor visits for example, will also be sensitive and subject to confidentiality constraints.

Traditionally, when companies sought to protect their computer systems and the information stored on those systems, they focused on the unauthorized interception of data transmissions and the unauthorized entry into the system. To combat the unauthorized interception of electronic transmissions, companies developed or purchased communication protocols that employed well-established, sophisticated encryption tools that encrypted data prior to its transmission. To prevent the unauthorized access of its computer system, companies installed complex firewalls to intercept transmissions before they entered the system in order to determine whether the sender had authorization to access the system. Authorization may take the form of a user account and password (or passwords), possession of a smart card, or possession of a computer disc for example.

Unfortunately, these programs fail to fully protect the information stored on a computer system. In particular, because they focus on events that occur outside of the computer system, the programs or methods are of little use when an attack comes from inside the organization. A program that encrypts data only before it is transmitted will not prevent a disgruntled employee from reading clear text information that resides on the network's storage devices. Likewise, a program that prevents unauthorized access to a network-will not prevent someone with authorization gained through fraud from reading clear text information that resides on the network's storage devices.

Of course, all data could be encrypted before it is stored on a storage device. Depending on the level of encryption, this action would likely prevent unauthorized persons from reading the information. Unfortunately, this process is not practical in many circumstances because decrypting large quantities of heavily encrypted data is time-consuming. Also, certain types of data or records are in continual or heavy demand because of the need to search the records or compile statistics about the information contained therein. Requiring decryption every time someone wanted to analyze or search the data would introduce unnecessary and significant delays into the process. For example, with regard to the medical profession, pharmaceutical companies may be interested in information concerning the usage of certain drugs, that is, how often the drugs are prescribed, the dosages, and the length of the prescription. Often, knowledge of patient information is not necessary for studies of this type. Therefore, it would be convenient if patient information and patient records were stored separately and the link between the information and records was hidden so that the records could be accessed without the need for decryption and without revealing confidential or sensitive patient information.

Therefore, a system and method are needed to protect information or data stored on a storage device from unauthorized access. The system or method, however, should not add significantly to the overall operating or performance cost of the system.

BRIEF SUMMARY OF THE INVENTION

The present invention provides a computer-based system and method for "dis-identifying" personal identifiable information (PII) and associated records (AR). More specifically, the system and method provide for storing related sensitive portions of the personal identifiable information (SPII), non-sensitive portions of the personal identifiable information (NSPII), and associated records in separate databases with each database record including additional entries that can be used to determine the related records or information in one of the other databases. The additional entries are encrypted so that the relationship between the database records is hidden. In one embodiment, the SPII, NSPII, and AR, are stored in plain text so that they may be more easily utilized.

In a preferred embodiment, the system of the present invention is implemented with a computer program, stored on a computer readable medium for directing operation of a computer, and generally includes a system manager module that is operable to communicate with a client terminal, an encryption and key management module, and a storage module in a computer environment. In one embodiment, the system manager communicates with the client terminal, the encryption module, and/or the storage module over a network. The system manager is operable to request and receive a hidden link from the encryption and key management module. The system manager is further operable to provide data to the encryption and key management module, to request the encryption or decryption of the data, and to receive the results of the encryption or decryption. The system manager is also operable to communicate information to the storage module for storage, to generate and is sue search queries to the storage module, and to receive the results of these search queries from the storage module.

The storage module is operable to receive information from the system manager module and to store that information in one of three databases or tables. The storage module will store the SPII in a SPII table, the NSPII in a NSPII table, and the AR in an AR table. The storage module will also store one or more hidden links and/or encrypted hidden links with each SPII, NSPII, and AR record. The storage module is further operable to receive and execute search queries and to communicate the results of the search queries. In a preferred embodiment, the storage module includes three physically separate and/or isolated storage devices with each device containing one of the tables or databases.

The system also includes an encryption and key management module. The encryption and key management module is operable to produce a hidden link and to encrypt or decrypt data. In one embodiment, the encryption and key management module is physically separate from the storage module and system manager module. In addition, in one embodiment, the key database is physically separate and/or isolated from the remaining portions of the encryption and key management module and from the storage module and system manager module.

The present invention also includes a method for storing the PII and AR. Initially, the PII is separated into SPII and NSPII. Next, a first hidden link $HL_{Di}$ is obtained. Thereafter, the SPII and the $HL_{Di}$ are inserted into a SPII database record. $HL_{Di}$ is then sent for encryption, which produces $E_{Di}(HL_{Di})$. Next, the AR and $E_{Di}(HL_{Di})$ are inserted into one or more AR database records. Thereafter, a second hidden link $HL_{Ri}$ is obtained, and $HL_{Di}$ is encrypted a second time to produce $E_{Ri}(HL_{Di})$. The NSPII, $HL_{Ri}$, and the two versions of the encrypted first hidden link, $E_{Di}(HL_{Di})$ and $E_{Ri}(HL_{Di})$, are then inserted into an NSPII database record.

The present invention also includes a method for retrieving the AR records related to a particular PII. First the hidden link $HL_{Di}$ stored with the SPII record for the PII is retrieved. $HL_{Di}$ is then sent for encryption, and the resulting $E_{Di}(HL_{Di})$ is used to find the desired AR records.

The present invention also includes a method for retrieving an SPII record related to an AR record. First, the encrypted hidden link $E_{Di}(HL_{Di})$ stored with the AR record is retrieved and used to find the NSPII record that is related to the desired SPII record. Next, the hidden link $HL_{Ri}$ and the encrypted hidden link $E_{Ri}(HL_{Di})$ stored with the NSPII record are retrieved. $E_{Ri}(KL_{Di})$ is sent for decryption, which produces $HL_{Di}$. Thereafter, $HL_{Di}$ is used to find the desired SPII record.

BRIEF DESCRIPTION OF THE DRAWINGS

Further features of the present invention will become apparent to those skilled in the art to which the present invention relates from reading the following description with reference to the accompanying drawings, in which:

FIG. 3 is a block diagram showing the SPII, NSPII and AR tables;

FIG. 4 is a block diagram showing tables that include a patient's sensitive information, non-sensitive information, and prescription information;

DETAILED DESCRIPTION OF THE INVENTION

The present invention encompasses a system and method for "dis-identifying" personal identifiable information (PII) and associated records (AR), in a computer environment. Pursuant to the system of the present invention, sensitive personal identifiable information (SPII), such as a patient's name and address, non-sensitive personal identifiable information (NSPII), such as a patient's age, and associated records (AR), such as the medication prescribed to a patient on a specific day, are inserted into separate databases and the link between the database records is hidden. Because there is no identifying information in the associated records or a link directly to identifying information, the records are dis-identified. The method of the present invention includes steps for storing SPII, NSPII, and AR and the hidden links associated with SPII, NSPII, and AR in separate databases. The method further includes steps for retrieving the SPII for a given AR and for retrieving the AR associated with a given SPII.

Figure 1:
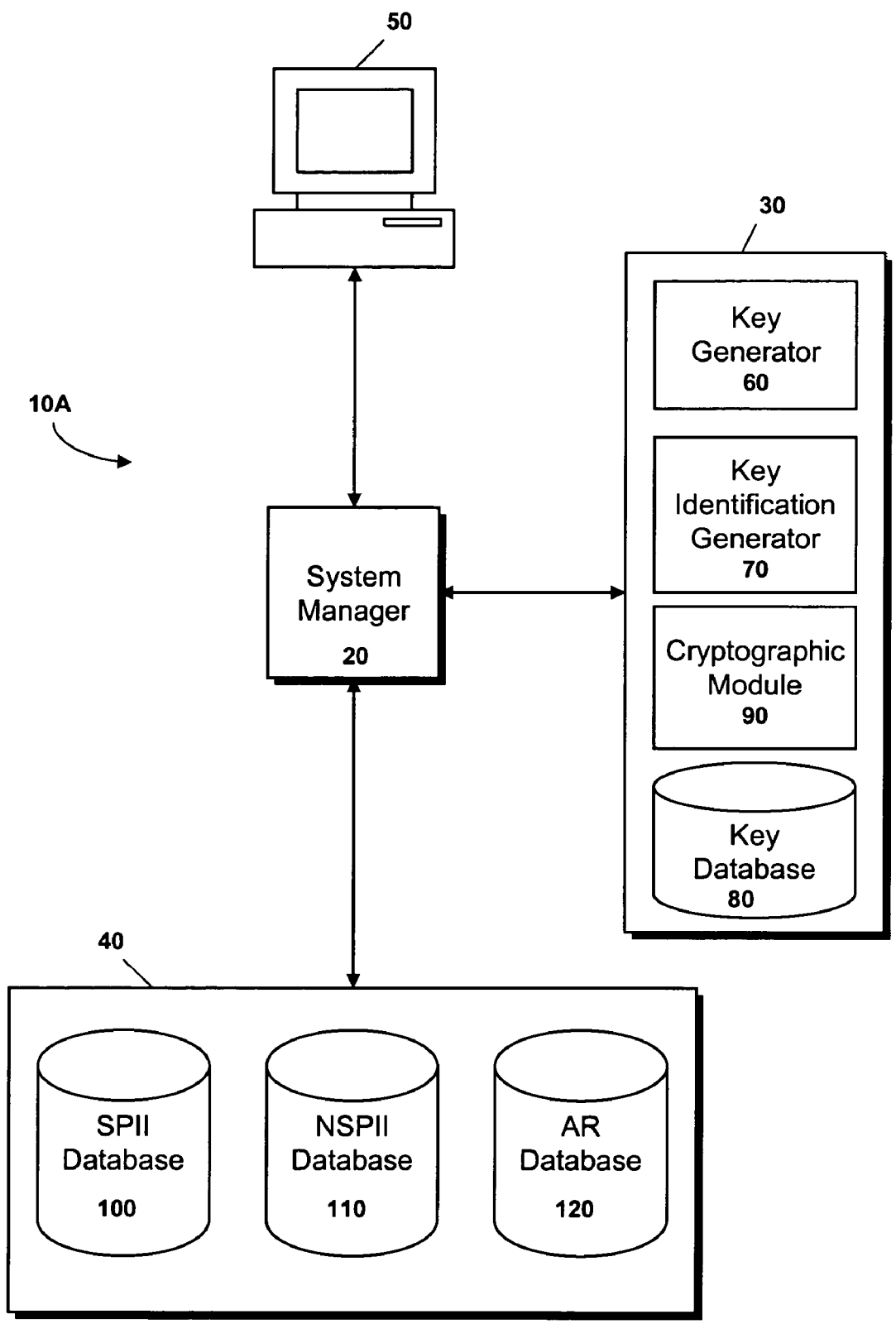
FIG. 1 is a schematic diagram of a computer system according to one embodiment of the present invention.

Referring first to FIG. 1, shown is a system 10A according to one embodiment of the present invention. The system 10 includes a system manager module 20 that is coupled to an encryption and key management module 30 and a storage module 40. The system manager module 20 is also coupled to a client terminal 50.

Generally, the system manager module 20 is operable to communicate with the client terminal 50, to interact with an encryption and key management module 30, and to interact with the storage module 40. Thus, the system manager module 20 includes one or more communications interfaces or devices, such as a graphical user interface or a network connector and software driver. In a preferred embodiment, the system manager module 20 includes one or more objects in an object-oriented computing environment. In this embodiment, the one or more objects may include an input object operable to insert SPII and NSPII into storage module 40, an input object operable to insert AR for a given SPII into storage module 40, a traverse object operable to retrieve SPII for a given AR from storage module 40, and a traverse object operable to retrieve the AR for a given SPII from storage module 40. In another embodiment, the system manager module 20 is a computer, and, as such, also includes a central processing unit and one or more memory devices containing computer executable instructions. In a further embodiment, the system manager module 20 includes computer executable instructions contained in the memory of a computer such as a server.

The encryption and key management module 30 also includes one or more communications interfaces or devices, such as a graphical user interface or a network connector and software driver. In a manner similar to the system manager module 20, in one embodiment, the encryption and key management module 30 is a computer, and, as such, also includes a central processing unit and one or more memory devices containing computer executable instructions. The encryption and key management module 30 may also consist of computer executable instructions contained in the memory of a computer such as a server. The encryption and key management module 30 may also include one or more objects in an object-oriented computing environment. In this embodiment, the objects would operate to perform the functions discussed below for the key generator 60, the key identifier 70, and the cryptographic module 90.

Continuing with FIG. 1, the encryption and key management module 30 includes a key generator 60, a key identifier generator 70, a key database 80, and an cryptographic module 90. The key generator 60 is operable to generate an encryption key, such as a triple data encryption standard (3DES) key. The key identifier generator 70 is operable to generate a unique number or other reference to a specific encryption key generated by the key generator 60. Preferably, the key identifier generator 70 is a hardware random number generator. It should be understood that the key generator 60 may include the ability to generate key identifiers which would eliminate the need for key identifier generator 70. The key database 80 resides on a memory device and preferably will have the form of a database or table having two columns and multiple rows. The columns of the key database 80 will store encrypted encryption keys and their associated key identifiers which will be provided by the key generator 60 and the key identifier generator 70. The key database 80 includes functionality that allows for receiving a search query that includes a key identifier and returning the encryption key associated with the key identifier. The cryptographic module 90 is further operable to receive data and to provide the data either encrypted or decrypted.

Encryption and key management module 30 is also operable to produce hidden links, to encrypt hidden links and to decrypt an encrypted hidden link. Stated generally, to produce a hidden link, key generator 60 generates an encryption key and key identification generator 70 a key ID. Thereafter, cryptographic module 90 encrypts the key ID, and the encrypted key ID is then returned as the hidden link. When $HL_{Di}$ is returned for encryption using encryption key Di (as will be described below), cryptographic module 90 will decrypt the hidden link to reveal the key ID for encryption key Di. The module 30 will then find encrypted encryption key Di in key database 80 using the key ID, and cryptographic module 90 will use encryption key Di to encrypt $HL_{Di}$. If $HL_{Di}$ is submitted for encryption using encryption key Ri, the hidden link $HL_{Ri}$ is used to find encryption key Ri in the same manner as just described. Similarly, when $E_{Ri}(HL_{Di})$ is submitted for decryption, $L_{Ri}$ is used to find encryption key Ri. One device that would serve as an encryption and key management module 30 for this invention is disclosed in International Publication Number WO 03/098864 A1, which was filed with the World Intellectual Property Organization and which is assigned to the assignee of the present invention. International Publication Number WO 03/098864 A1 is incorporated fully herein by reference.

The storage module 40 includes an SPII database 100, a NSPII database 110, and an AR database 120. Preferably, each database 100, 110, 120 resides on a separate, physically isolated database server. Like the key database 80, the storage module 40 includes functionality that allows for receiving a query seeking certain information and returning the information sought. Also, storage module 40 includes one or more communications interfaces or devices, such as a graphical user interface or a network connector and software driver.

FIG. 3 shows a functional embodiment of the SPII database 100, the NSPII database 110, and the AR database 120. Each row of the SPII table 150 includes multiple columns 152 containing sensitive personal identifiable information and a column 154 containing the hidden link $HL_{Di}$. As mentioned above, SPII may include the name, address, telephone number, and social security number of a patient. Each row of the NSPII table 160 includes multiple columns 162 of non-sensitive personal identifiable information such as gender, height, weight, age, race, and marital status which may have clinical value when correlated to AR's. Each row of the NSPII table 160 also contains two columns 164, 166 containing the encrypted hidden links $E_{Di}(HL_{Di})$ and $E_{Ri}(HL_{Di})$, and a column 168 containing the hidden link $HL_{Ri}$. Finally, each row of the AR table 170 includes multiple columns 172 containing the information of the associated records, such as prescription information, and a column 174 containing the encrypted hidden link $E_{Di}(HL_{Di})$. The hidden links $HL_{Di}$ and $HL_{Ri}$ and the encrypted hidden links $E_{Di}(HL_{Di})$ and $E_{Ri}(HL_{Di})$ will be explained in greater detail below.

FIG. 4 shows the tables of FIG. 3 as they may be used in a medical application. In this figure, the SPII table 150 is entitled "Patient Table (sensitive information)." SPII columns 152 include columns for a patient's name 152a, address 152b, social security number 152c, and date of birth 152d. The hidden link column 154 remains the same. The NSPII table 160 is entitled "Patient Table (non-sensitive information)." In this table 160, NSPII column 162 includes columns for a patient's sex 162a, age 162b, marital status (M/S) 162c, and race 162d. The columns containing the encrypted hidden links $E_{Di}(HL_{Di})$ and $E_{Ri}(HL_{Di})$ 164, 166 and the hidden link $HL_{Ri}$ 168 remain the same. The AR table 170 is entitled "Prescription Table." The AR column 172 includes a column for a date 172a, a drug (Rx) 172b, a strength 172c, a dose 172d, and a quantity 172e). The column containing the encrypted hidden link $E_{Di}(HL_{Di})$ 174 remains the same.

Continuing now with FIG. 1, the client terminal 50 generally includes a central processing unit, a data entry mechanism, such as keyboard or a pointing device (i.e., a mouse), and a display. The client terminal 50 also includes one or more communications interfaces or devices, such as a graphical user interface, a modem, or a network connector and software driver. The central processing unit is operable to receive input from the data entry mechanism, to receive and send information via the communication interface or device, and to control the monitor. The central processing unit may also control other computer devices such as a printer or disc drive.

Figure 2:
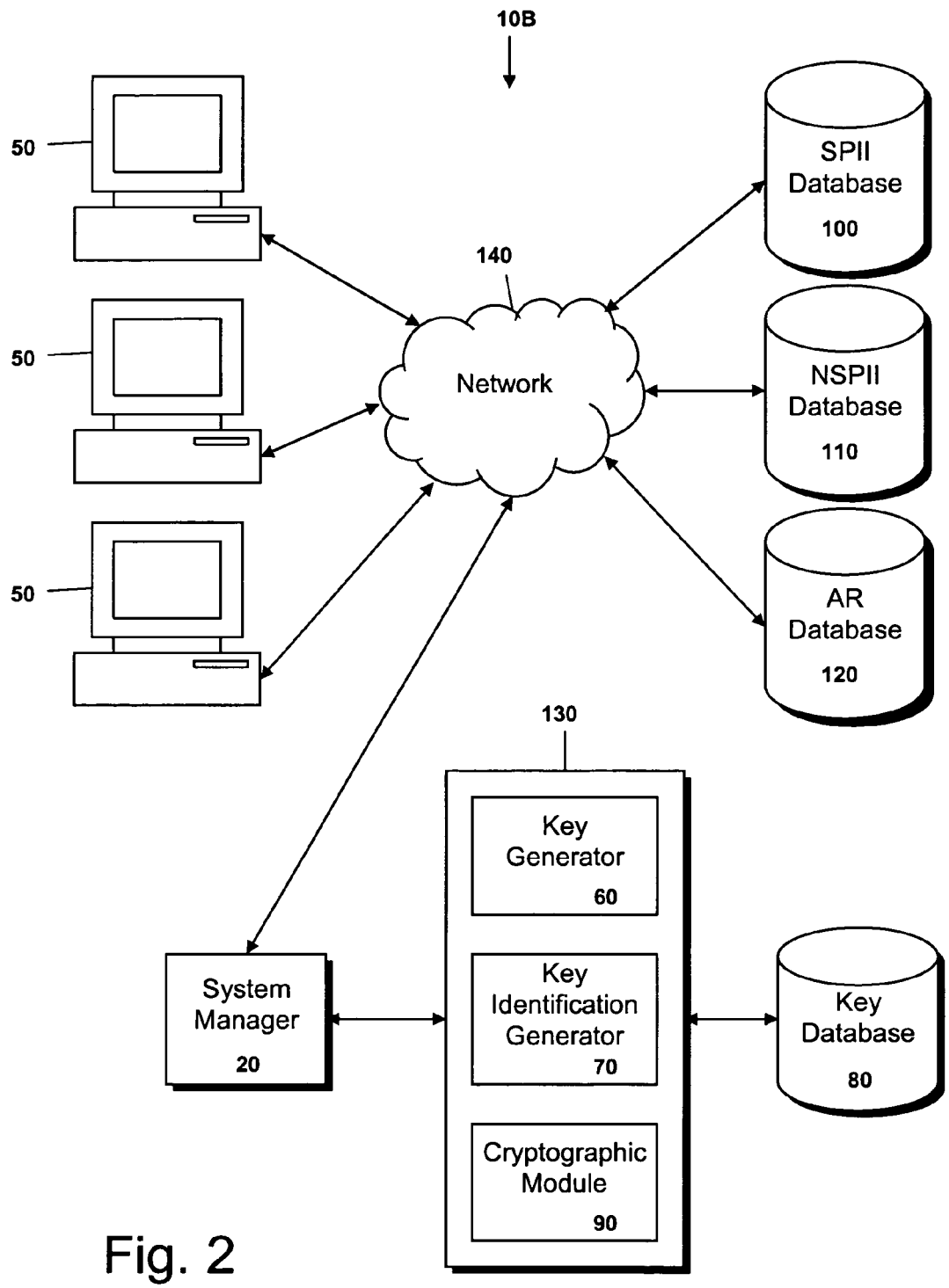
FIG. 2 is a schematic diagram of a system according to another embodiment of the present invention.

A second embodiment 10B of the system of the present invention is shown in FIG. 2. In this embodiment 10B, a number of client terminals 50, the system manager module 20, the SPII database 100, the NSPII database 110, and the AR database 120 are connected to a network 140. Thus, each of the terminals 50, the system manager module 20, the SPII database 100, the NSPII database 110, and the AR database 120 include communication interfaces or devices that provide for network communication. The network 140 may be, for example, the Internet, a local area network, or a wide area network.

The embodiment 10B shown in FIG. 2 also includes an encryption and key management module 130 that includes a key generator 60, a key identifier generator 70, and an cryptographic module 90. Notably, the key database 80 is physically separate and isolated from encryption and key management module 130 for additional security. Also, the embodiment 10B does not include a separate storage module 40. Instead, the SPII database 100, the NSPII database 110, and the AR database 120 are also physically separate, isolated database devices. The key database 80 and the SPII database 100, the NSPII database 110, and the AR database 120 all consist of memory devices such as a database server and all are operable to receive a search request and return the information sought.

Figure 5:
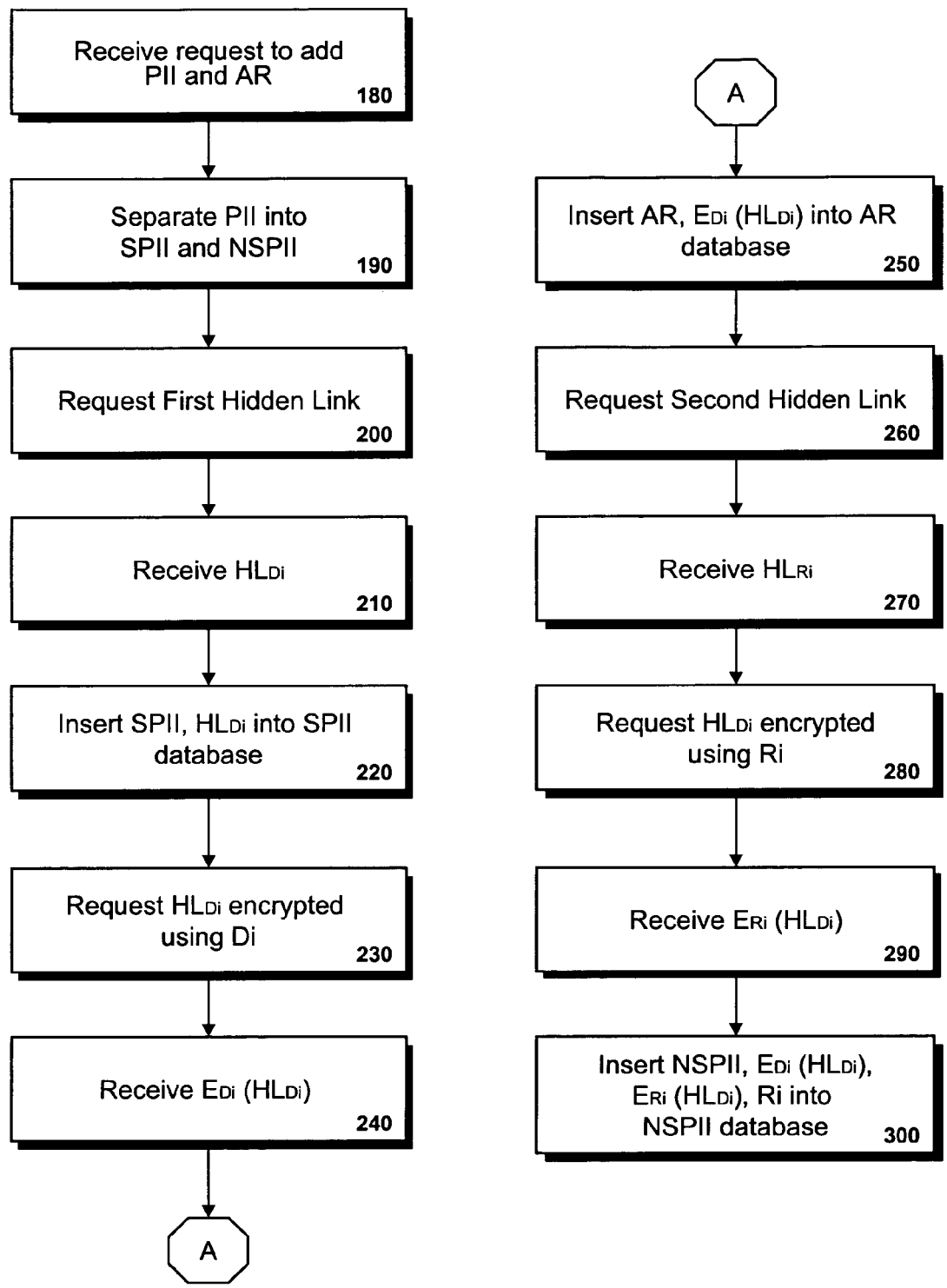
FIG. 5 is a flowchart showing a method for storing sensitive information and associated records.

Referring now to FIG. 5, the present invention also includes a method for storing personal identifying information and associated records. Initially, in box 180, a request to add a PII and associated records AR is received. It should be understood that the request includes the information that comprises the PII and the AR or includes information, such as a file name, that points to the PII and AR. Next, in box 190, the PII is separated into SPII and NSPII. In box 200, a first hidden link is requested, for example from an encryption and key management module 30, 130, and, in box 210, hidden link $HL_{Di}$ is received. Thereafter, in box 220, the SPII and the first hidden link $HL_{Di}$ are inserted into a record in the SPII database 150. In the preferred embodiment, the SPII is stored in clear text. In an alternate embodiment, the SPII is encrypted using encryption key Di before it is stored.

Continuing with FIG. 5, after storing the SPII, a request is sent to encrypt $HL_{Di}$ using the first encryption key Di in box 230. Next, in box 240 $E_{Di}(HL_{Di})$ is received. In box 250, the associate records AR are inserted in the AR database 170 with each row or record also including $E_{Di}(HL_{Di})$. As stated above, in the preferred embodiment, the AR is stored in clear text, while in an alternate embodiment, the AR is encrypted using encryption key Di before it is stored.

In box 260, a request for second hidden link is sent, and, in box 270, $HL_{Ri}$ is received. In box 280, a request is sent to encrypt $HL_{Di}$ using the second encryption key Ri and, in box 290, $E_{Ri}(HL_{Di})$ is received. Finally, in box 300, the NSPII, the second hidden link Ri, and the two versions of the encrypted first hidden link, $E_{Di}(HL_{Di})$ and $E_{Ri}(HL_{Di})$, are inserted into a record in the NSPII database. Again, in the preferred embodiment, the NSPII is stored in clear text, while in an alternate embodiment, the NSPII is encrypted using encryption key Di before it is stored.

Figure 6:
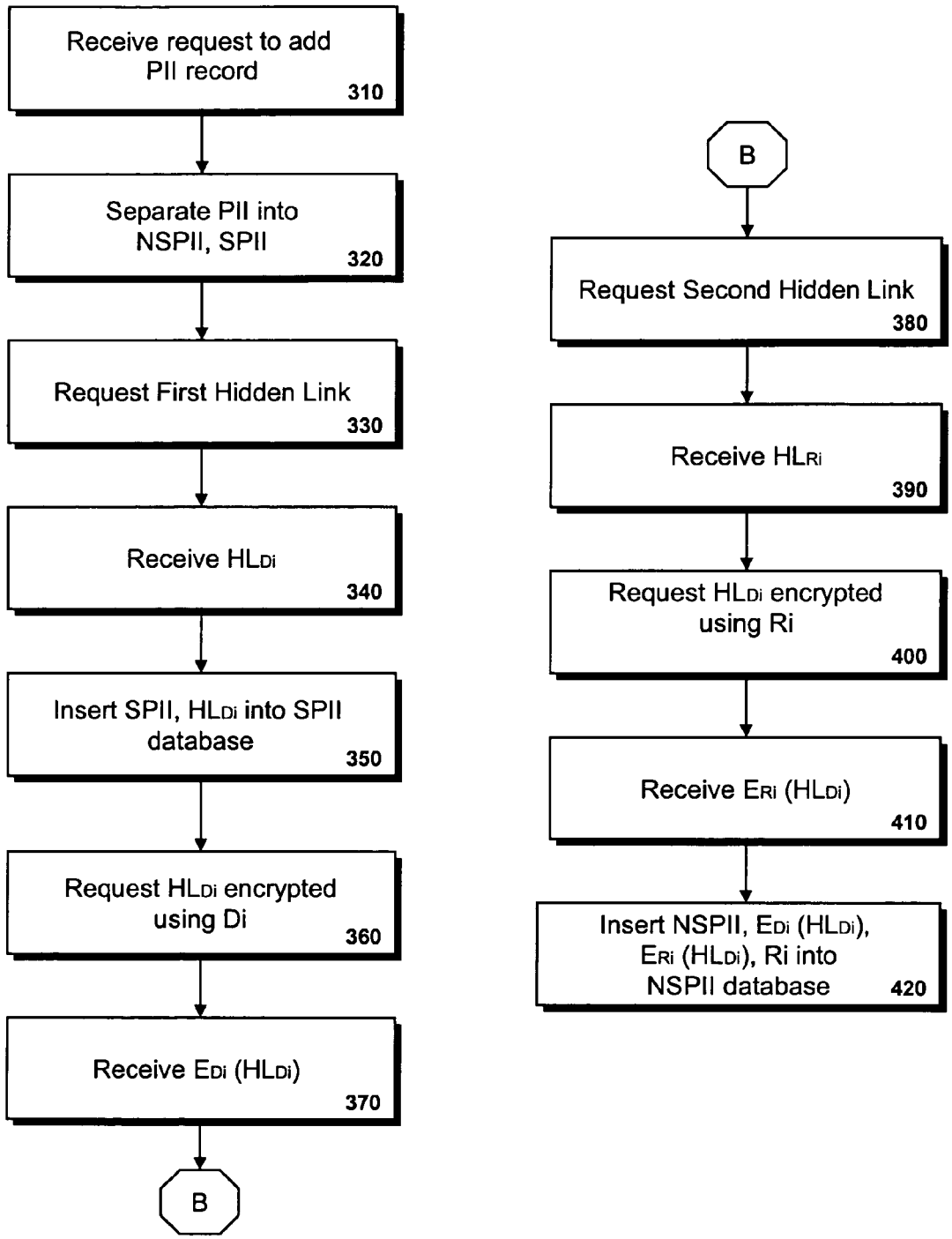
FIG. 6 is a flowchart showing a method for storing sensitive information.

FIG. 6 shows a flowchart depicting a method for storing personal identifiable information PII Initially, in box 310, a request to add a PII record is received. It should be understood that the request includes the information comprising the PII or information pointing to the PII. Next, in box 320, the PII is separated into SPII and NSPII. In box 330, a first hidden link is requested, and, in box 340, $HL_{Di}$ is received. Thereafter, in box 350, the SPII and the first hidden link $HL_{Di}$ are inserted into a record in the SPII database 150.

Continuing with FIG. 6, after storing the SPII, a request is sent to encrypt $HL_{Di}$ using the first encryption key Di in box 360. Next, in box 370, $E_{Di}(HL_{Di})$, is received. In box 380, a request for second hidden link is sent. Thereafter, in box 390, $HL_{Ri}$ are received. In box 400, a request is sent to encrypt $HL_{Di}$ using the second encryption key Ri and, in box 410 $E_{Ri}(HL_{Di})$ is received. Finally, in box 420, the NSPII, the second hidden link $HL_{Ri}$, and the two versions of the encrypted first hidden link, $E_{Di}(HL_{Di})$ and $E_{Ri}(HL_{Di})$, are inserted into a record in the NSPII database.

Figure 7:
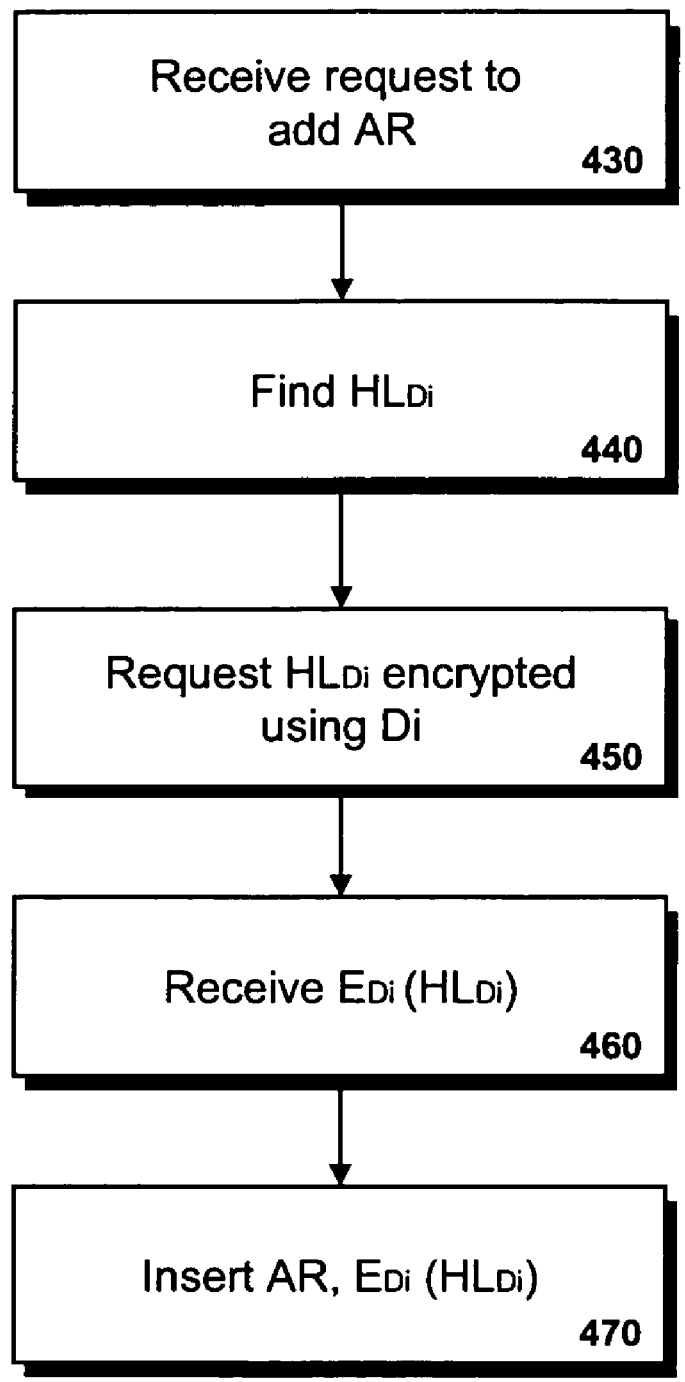
FIG. 7 is a flowchart showing a method for storing associated records.

FIG. 7 shows a flowchart depicting a method for storing associated records AR. First, in box 430, a request is received to add one or more AR's related to specific PII entry. It should be understood that the request includes the information comprising at least the SPII and the AR. In box 440, the SPII is used to lookup the hidden link $HL_{Di}$ associated with the SPII. Thereafter, in box 450, a request is sent to encrypt $HL_{Di}$ using encryption key Di, and in box 460, $E_{Di}(HL_{Di})$ are received.

Finally, in box 470, the associate records AR are inserted into a record in the AR database 170 with each row or record also including $E_{Di}(HL_{Di})$.

Figure 8:
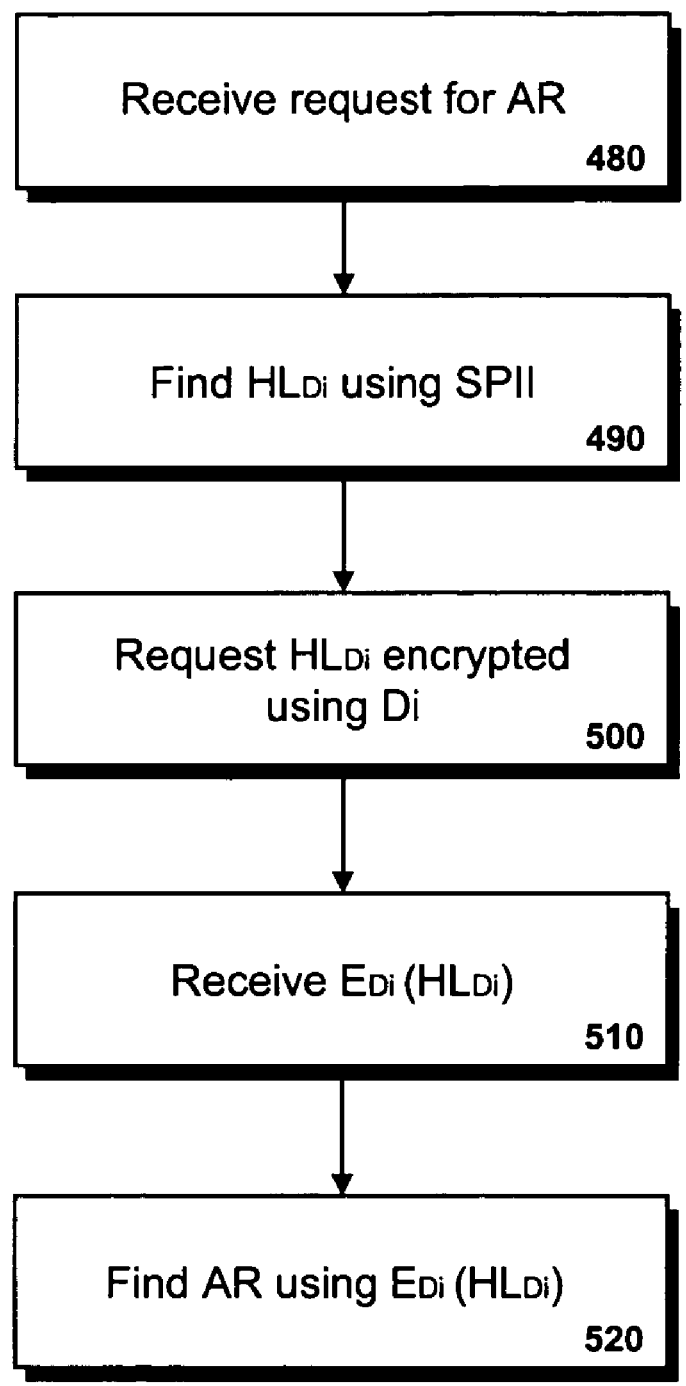
FIG. 8 is a flowchart showing a method for retrieving sensitive information.

Referring now to FIG. 8, the present invention also includes a method for retrieving AR related to a particular PII. In box 480, a request is received to retrieve the associated records AR for a particular PII. The request includes the specifics of the PII including the SPII. Next, in box 490, the hidden link $HL_{Di}$ stored with the SPII is retrieved, for example by issuing a search query containing one or more portions of the SPII to the SPII database 150. Thereafter, in box 500, a request is made to encrypt $HL_{Di}$ using encryption key Di, and, in box 510, $E_{Di}(HL_{Di})$ is received. Finally, in box 520, $E_{Di}(HL_{Di})$ is used to find the associated records for that include $E_{Di}(HL_{Di})$, for example by issuing a search query containing $E_{Di}(HL_{Di})$ to the AR database 170.

Figure 9:
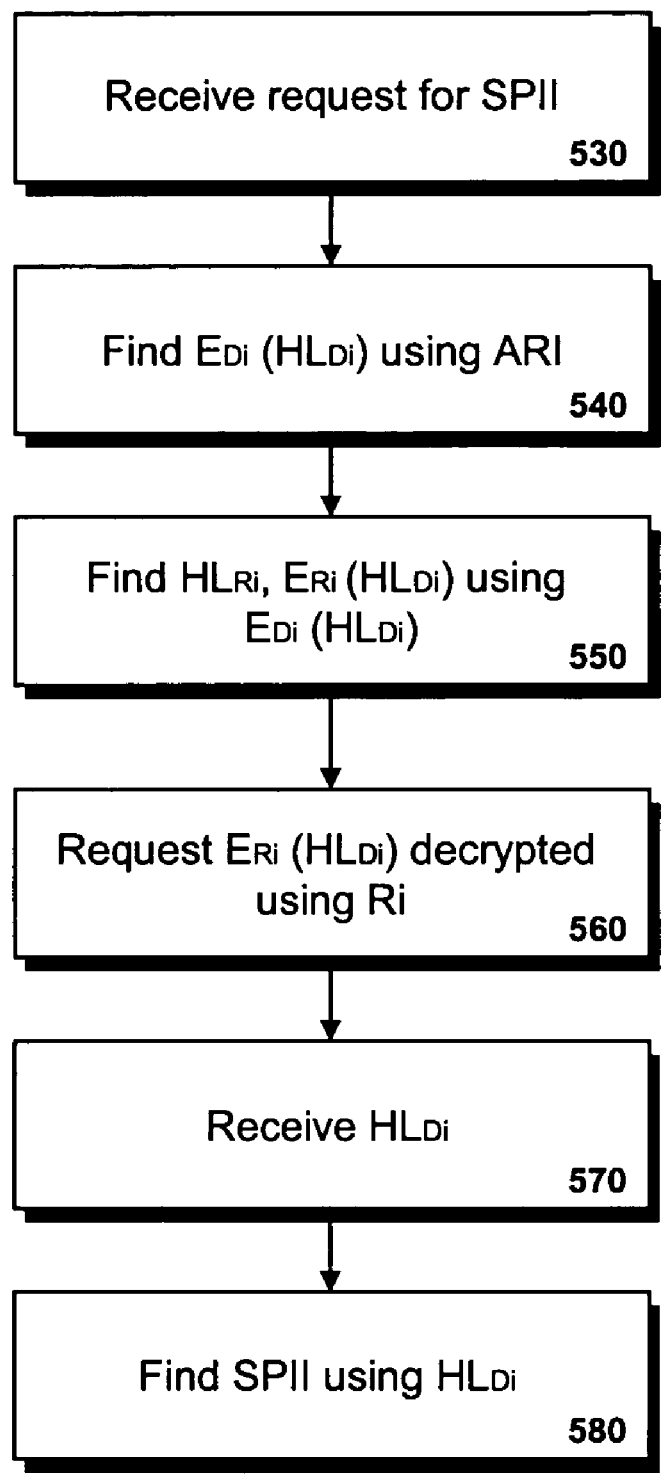
FIG. 9 is a flowchart showing a method for retrieving associated records.

As shown in FIG. 9, the present invention also includes a method for retrieving SPII related to an AR. In box 530, a request for the SPII related to an associated record AR is received. Necessarily, the request includes the AR. In box 540, the encrypted hidden link $E_{Di}(HL_{Di})$ stored with the AR is retrieved, for example by issuing a search query containing information contained in the AR to the AR database 170. Next, in box 550, the hidden link $E_{Di}(HL_{Di})$ is used to find the NSPII entry that is related to the SPII entry for example by issuing a search query containing $E_{Di}(HL_{Di})$ to the NSPII database 160. The hidden link $HL_{Ri}$ and the encrypted hidden link $E_{Ri}(HL_{Di})$ are retrieved from the NSPII record associated with the $E_{Di}(HL_{Di})$. Thereafter, in box 560, a request to decrypt the second encrypted hidden link $E_{Ri}(HL_{Di})$, and, in box 570, $HL_{Di}$ is received. Finally, in box 580, the hidden link $HL_{Di}$ is used to find the desired SPII for example by issuing a search query containing $HL_{Di}$ to the SPII database 150.

From the above description of preferred embodiments of the invention, those skilled in the art will perceive improvements, changes and modifications. Such improvements, changes and modifications within the skill of the art are intended to be covered by the appended claims.

Having described at least one preferred embodiment of the invention, what is claimed is:

1. A system for protecting the relationship between personal identifiable information and one or more associated records, the system comprising:
   a processor,
   a system manager module operably residing on the processor, the manager module operable to receive a hidden link and an encrypted hidden link from an encryption module, to insert the personal identifiable information and the associated records into separate databases in a storage module, and to retrieve the personal identifiable information and the associated records from the separate databases, wherein the personal identifiable information and the associated records are stored with one or more hidden links or encrypted hidden links so that there is no direct link between the personal identifiable information and the associated records,
   and further wherein the personal identifiable information includes a sensitive information portion and a non-sensitive information portion and wherein the system manager module is operable to separate the personal identifiable information into a sensitive information portion and a non-sensitive information portion, to insert the sensitive information and the non-sensitive information portions into separate databases, and to retrieve the sensitive information and the non-sensitive information portions from their separate databases, and further wherein an entry in the sensitive information database includes a first hidden link, the first hidden link associated with a first encryption key, and each entry in the associated records database and the non-sensitive information database related to the entry in the sensitive information database include the first hidden link encrypted according to the first encryption key, and wherein the non-sensitive information database further includes a second hidden link, the second hidden link associated with a second encryption key, and the first hidden link encrypted according to the second encryption key.

2. The system of claim 1 further including an encryption and key management module operable to generate a hidden link and to encrypt and decrypt data.

3. The system of claim 2 wherein the encryption and key management module further includes a key database and wherein the encryption and key management module stores encrypted encryption keys and associated key identifiers in the key database.

4. The system of claim 2 further including a key database that is physically separate from the encryption module, the key database operable to store encrypted encryption keys and associated key identifiers.

5. The system of claim 1 further including a storage module, the storage module including databases for the personal identifiable information and associated records.

6. The system of claim 1 further including a storage module, the storage module including a sensitive information database, a non-sensitive information database, and an associated records database.

7. The system of claim 6 wherein each database in the storage module is physically separated from the remaining databases.

8. The system of claim 6 wherein each database in the storage module resides on a separate database server.

9. The system of claim 1 further including at least one client terminal in communication with the system manager module.

10. The system of claim 1 wherein the personal identifiable information and the associated records are stored in clear text.

11. The system of claim 1 wherein the personal identifiable information and the associated records are encrypted before they are stored.

12. A method in a computer system for storing personal identifiable information and associated records so that there is no direct link between the personal identifiable information and the associated records, the personal identifiable information including sensitive information and non-sensitive information, the computer system including a sensitive information database, a non-sensitive information database, and an associated records database, the method comprising:
  separating the personal identifiable information into sensitive information and non-sensitive information;
  obtaining a first hidden link, the first hidden link associated with a first encryption key;
  inserting the sensitive information and the first hidden link into the sensitive information database;
  receiving the first hidden link encrypted using the first encryption key;
  inserting the associated records and the first hidden link encrypted using the first encryption key into the associated records database;
  obtaining a second hidden link associated with a second encryption key;
  receiving the first hidden link encrypted using the second encryption key;
  inserting the non-sensitive information, the first hidden link encrypted according to the first encryption key, the second hidden link, and the first hidden link encrypted according to the second encryption key into the non-sensitive information database.

13. The method of claim 12 wherein the hidden links are generated by an encryption and key management module.

14. The method of claim 12 further including receiving a request to store personal identifiable information and associated records, the request containing the information that comprises the personal identifiable information and associated records.

15. The method of claim 14 wherein the request is received from a client terminal.

16. The method of claim 12 further including sending the personal identifiable information and associated records for encryption with the first encryption key and wherein the encrypted personal identifiable information and associated records are inserted into the databases.

17. A computer readable medium containing computer executable instructions for performing a method, the method comprising
  separating the personal identifiable information into sensitive information and non-sensitive information;
  receiving a first hidden link, the first hidden link associated with a first encryption key;
  inserting the sensitive information and the first hidden link into the sensitive information database;
  receiving the first hidden link encrypted using the first encryption key;
  inserting the associated records and the first hidden link encrypted using the first encryption key into the associated records database;
  receiving a second hidden link, the second hidden link associated with a second encryption key;
  receiving the first hidden link encrypted using the second encryption key;
  inserting the non-sensitive information, the first hidden link encrypted according to the first encryption key, the second hidden link, and the first hidden link encrypted according to the second encryption key into the non-sensitive information database.

18. A method in a computer system for retrieving the sensitive information portion of a personal identifiable information related to certain associated records, the sensitive information stored in a sensitive information database along with a first hidden link, the first hidden link associated with a first encryption key, and the associated records stored in an associated records database along with the first hidden link encrypted using the first encryption key so that there is no direct link between the sensitive personal identifiable information and the associated records, the personal identifiable information further including a non-sensitive information portion stored in a non-sensitive information database along with the first hidden link encrypted using the first encryption key, a second hidden link associated with a second encryption key, and the first hidden link encrypted using the second encryption key, the method comprising:
  retrieving the first hidden link encrypted with the first encryption key stored with the associated record;
  using the first hidden link encrypted with the first encryption key stored with the associated record to find the record in the non-sensitive database related to the associated record;

retrieving the second hidden link and the first hidden link encrypted with the second encryption key stored with the non-sensitive database record from the non-sensitive database record;

submitting the first hidden link encrypted with the second encryption key for decryption thereby receiving the first hidden link; and using the first hidden link to retrieve the sensitive portion of the personal identifiable information from the sensitive information database.

19. The method of claim 18 wherein retrieving the first hidden link encrypted with the first encryption key stored with the associated record comprises forming a search request that includes information in the associated record; transmitting the search request to the associated record database; and receiving the first hidden link encrypted with the first encryption key stored with the associated record from the associated record database.

20. The method of claim 18 wherein using the first hidden link encrypted with the first encryption key stored with the associated record to find the record in the non-sensitive database related to the associated record comprises forming a search request that includes the first hidden link encrypted with the first encryption key stored with the associated record and transmitting the search request to the non-sensitive information database.

21. The method of claim 18 wherein retrieving the sensitive portion of the personal identifiable information from the sensitive information database comprises forming a search request that includes the hidden link associated with the record for the sensitive portion of the personal identifiable information in the sensitive information database; transmitting the search request to the sensitive information database; and receiving the sensitive portion of the personal identifiable information from the sensitive information database.

22. A computer readable medium containing computer executable instructions for performing a method, the method comprising:

retrieving the first hidden link encrypted with the first encryption key stored with the associated record;

using the first hidden link encrypted with the first encryption key stored with the associated record to find the record in the non-sensitive database related to the associated record;

retrieving the second hidden link and the first hidden link encrypted with the second encryption key stored with the non-sensitive database record from the non-sensitive database record;

submitting the first hidden link encrypted with the second encryption key for decryption thereby receiving the first hidden link; and using the first hidden link to retrieve the sensitive portion of the personal identifiable information from the sensitive information database.

\* \* \* \* \*